United States Patent
Katayama et al.

(10) Patent No.: US 6,410,749 B1
(45) Date of Patent: Jun. 25, 2002

(54) PROCESS FOR THE PREPARATION OF OPTICALLY ACTIVE AMINO ALCOHOLS

(75) Inventors: Eiji Katayama, Odawara; Daisuke Sato, Odawara; Hirohito Ooka, Hadano; Tsutomu Inoue, Chigasaki, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/889,595

(22) PCT Filed: Jan. 18, 2000

(86) PCT No.: PCT/JP00/00183

§ 371 (c)(1), (2), (4) Date: Jul. 17, 2001

(87) PCT Pub. No.: WO00/41997

PCT Pub. Date: Jul. 20, 2000

(30) Foreign Application Priority Data

Jan. 18, 1999 (JP) ............................................ 11/009873

(51) Int. Cl.[7] ............................................ C07D 209/48
(52) U.S. Cl. ............................ 548/478; 560/22; 560/24; 560/28; 560/29; 560/30; 560/115; 560/157; 560/166; 564/82; 564/83; 564/98; 564/99; 564/159; 564/184; 564/185; 564/186; 564/218; 564/219; 564/224; 564/382; 568/880
(58) Field of Search ...................... 564/93, 159, 186, 564/224, 82, 83, 99, 98, 185, 184, 218, 219; 560/166, 24, 29, 30, 22, 28, 115, 157; 568/880; 548/478

(56) References Cited

U.S. PATENT DOCUMENTS

| 4,290,961 A | * | 9/1981 | Mestroni |
| 5,763,688 A | * | 6/1998 | Ikariya |
| 6,184,381 B1 | * | 2/2001 | Ikariya |

FOREIGN PATENT DOCUMENTS

| JP | 10-236986 A | * | 8/1998 |
| JP | 10-236986 | | 9/1998 |
| JP | 11-189558 | | 1/1999 |

* cited by examiner

*Primary Examiner*—Michael L. Shippen
(74) *Attorney, Agent, or Firm*—Dennis G. LaPointe; Mason & Associates, PA

(57) ABSTRACT

Process for preparing optically active β-amino alcohols represented by a general formula (2): Ra—C*H(OH)—C*H(Rb)—Rc wherein Ra and Rc are each independently hydrogen, optionally substituted alkyl, optionally substituted cycloalkyl, Rb is one member selected from among groups represented by the following general formulae; (3) R1CO(R2)N—, and (4) R1CO(R1'CO)N—, and C* is an asymmetric carbon atom, characterized by reacting a racemic α-aminocarbonyl compound represented by the general formula (1): Ra—CO—CH(Rb)—Rc, with hydrogen in the presence of an optically active transition metal compound represented by a general formula (7): MaXY(Px)m(Nx)n wherein Ma represents a metal atom belonging to VIII-group of the periodic law, X and Y represent each independently hydrogen, halogeno, Px represents a phosphine ligand, Nx represents an amine ligand, at least one of Px and Nx is optically active, and m and n each independently represent 0 or an integer of 1 through 4 and a base.

3 Claims, No Drawings

PROCESS FOR THE PREPARATION OF OPTICALLY ACTIVE AMINO ALCOHOLS

FIELD OF THE INVENTION

The present invention is related to a process to highly enantioselectively and highly diastereoselectively prepare optically active β-amino alcohols useful as an intermediate for synthesizing pharmaceutical active ingredients and agricultural chemicals at a high yield by using a racemic α-aminocarbonyl compound as the starting material.

BACKGROUND ART

Optically active β-amino alcohols are considered as an important intermediate for synthesizing pharmaceutical active ingredients and agricultural chemicals. As references wherein processes for preparing such optically active β-amino alcohols have been disclosed, the followings may be given as examples.
1. Process in which the reaction of α-(substituted-amino) aldehyde and a metal reagent is employed.
    i) JP laid-open No. 50-137911 gazette
        * (Anti-isomer/Syn-isomer=4.3–2.5/1)
    ii) J. Org. Chem., 55, 1439 (1990)
2. Process in which diastereoselective reduction of optically active α-amino ketone is employed.
    Tetrahedron. Lett., 35, 547 (1994)
3. Process in which diastereoselective reduction of optically active α-alkoxyimine is employed.
    J. Chem. Soc. Chem. Commun., 746 (1987)
4. Process in which diastereoselective hydrogenation of α-amino-β-keto acid is employed.
    i) J. Am. Chem. Soc., 111, 9134 (1989)
    ii) J. Am. Chem. Soc., 115, 144 (1993)
5. Process in which asymmetric reduction of keto oxime is employed.
    JP laid-open No. 10-45688 gazette Among the processes in the past as described above, the diastereoselctivity in the processes ① and ⑤ are low. The processes ② and ③ require to prepare the raw material for the optically active compound beforehand and are thus complicated, the process ④ allows to prepare highly diastereoselective optically active amino alcohol when a substrate containing a functional group, such as carboxyl, in the molecule is used, however, it is difficult to prepare optically active compounds according to the process ④ when simple amino alcohol containing no functional group in the molecule is used.

Because of the difficulty as described above, development of selective production process of optically active β-amino alcohols by using the racemic modification, which is more commonly-useful and can produce the desired products at high yields, has been desired.

In the present invention, the syn-isomer is defined as the one having a steric configuration wherein both amino group and hydroxy group to be respectively substituted in a vertical direction of carbon atoms in chain face toward the same plane when the carbon atoms in chain are fixed as the central axis and the steric configuration is laid in a horizontal direction, while the anti-isomer is defined as the one having a steric configuration wherein both amino group and hydroxy group face toward the contrary planes with each other.

DISCLOSURE OF INVENTION

It is an object of the present invention to provide practical manufacturing process for optically active α-amino alcohols by using one of widely-available racemic α-aminocarbonyl compounds as the starting material.

For achieving the object described above, the present invention provides a process for the preparation of optically active β-amino alcohols represented by the general formula (2); Ra—C*H(OH)—C*H(Rb)—Rc, wherein Ra and Rc are each independently hydrogen, optionally substituted alkyl, optionally substituted cycloalkyl, optionally substituted alkenyl, optionally substituted aralkyl or optionally substituted aryl, Rb is one member selected from among groups represented by the following general formulae; (3) R1CO(R2)N—, (4) R1CO(R1'CO)N—, (5) R1CO(R1'SO$_2$)N—, and (6) R1SO$_2$(R2)N—, wherein R1, R1' and R2 are each independently hydrogen, optionally substituted alkyl, optionally substituted alkoxy, optionally substituted cycloalkyl, optionally substituted cycloalkoxy, optionally substituted alkenyl, optionally substituted aralkyl, optionally substituted aralkyloxy, optionally substituted aryl or optionally substituted aryloxy, or alternatively R1 and R2 or R1 and R1' may be united to form a five- to eight-membered nitrogenous heterocycle, and C* is an asymmetric carbon atom, characterized by reacting a racemic α-aminocarbonyl compound represented by the general formula (1); Ra—CO—CH(Rb)—Rc, wherein Ra, Rb and Rc are each as defined above, with hydrogen or a hydrogen donor in the presence of an optically active transition metal compound and a base.

In the preparation process of optically active β-amino alcohols according to the present invention, it is preferable that the optically active transition metal compound is a homogeneous system optically active hydrogenation catalyst.

And, it is further preferable that the homogeneous system optically active hydrogenation catalyst is an optically active transition metal compound represented by the following general formula;

wherein Ma represents a metal atom belonging to VIII-group metals, X and Y represent each independently hydrogen, halogeno, carboxyl, hydroxide or alkoxy, Px represents phosphine ligand, Nx represents amine ligand, and at least either of Px or Nx is optically active, and m and n are an integer of 1 through 4.

Further, in the preparation process of optically active β-amino alcohols according to the present invention, it is preferable to use a compound represented by the following general formula (8);

wherein Mb represents either an alikali metal ion or an alkaline earth metal ion, Z represents OH$^-$, RO$^-$, wherein R is C$_{1-6}$ alkyl, an aromatic anion, HS$^-$ or CO3$^{2-}$, and m' and n' are an integer of 1 through 3, as the base described above. However, a quaternary amine salt compound may be used as the base as well.

According to the preparation process of optically active β-amino alcohols of the present invention, optically active β-amino alcohols useful as the intermediate for the synthesis of pharmaceutical active ingredients and agricultural chemicals and represented by the general formula (2) can be prepared highly selectively and at a high yield.

Now, the embodiments for carrying out the present invention are explained in the following.

As the raw material to be used in the process of the present invention, a compound represented by the following general formula (1);

Ra—CO—CH(Rb)—Rc (1)

is used.

In the general formula (1), Ra and Rc each independently represent hydrogen, optionally substituted alkyl, optionally substituted cycloalkyl, optionally substituted alkenyl, optionally substituted aralkyl or optionally substituted aryl.

In addition to the groups as described above, any of alkyl, alkenyl, aralkyl and aryl may be used as far as that may give no inhibitory effect on the reactions in the process of the present invention.

As substituents for the optionally substituted alkyl, the optionally substituted cycloalkyl, the optionally substituted alkenyl, the optionally substituted aralkyl and the optionally substituted aryl described above, any ones giving no inhibitory effect on the reactions in the process of the present invention may be used without limitation in terms of substitution position, type of substituent, numbers of substituents, etc.

As examples for the substituents, hydroxy, amino, nitro, alkyl, such as methyl, ethyl, propyl, isopropyl, butyl, sec-butyl, t-butyl, pentyl and hexyl; alkoxy, such as methoxy, ethoxy, propoxy, isopropoxy, butoxy and t-butoxy; alkoxycarbonyl, such as methoxycarbonyl, ethoxycabonyl, propoxycarbonyl, isopropoxycarbonyl, butoxycarbonyl and t-butoxycarbonyl; phenoxycarbonyl, phenyl optionally substituted at the arbitrary position on the benzene ring, naphthyl optionally substituted at the arbitrary position on the naphthalene ring, such as 1-naphthyl and 2-naphthyl, a heterocyclic group optionally substituted at the arbitrary position on the ring, such as furan, pyran, dioxolane, dioxane, pyrrole, thiophene, imidazole, pyrazole, oxazole, isoxazole, triazole, thiazole, isothiazole, pyridine, pyridazine, pyrazine, benzimidazole, benzopyrazole, benzothiazole and quinoline, and halogeno, such as fluorine, chlorine and bromine, may be given.

As examples for the optionally substituted alkyl and cycloalkyl, $C_{1-20}$ alkyl and $C_{3-8}$ cycloalkyl, such as methyl, ethyl, propyl, isopropyl, butyl, sec-butyl, tert-butyl, pentyl, isopentyl, neopentyl, tert-pentyl, hexyl, heptyl, octyl, nonyl, decyl, dodecyl, cyclopropyl, cyclobutyl, cyclopentyl and cyclohexyl, may be given.

As examples for the optionally substituted alkenyl, $C_{2-20}$ alkenyl, such as vinyl, 1-propenyl, 2-propenyl, 1-isopropenyl, 1-butenyl, 1-isopropenyl, 2-butenyl, 3-butenyl, 1,3-butadienyl, 1-pentenyl, 2-pentenyl and 3-pentenyl, may be given.

As examples for the optionally substituted aralkyl described above, $C_{7-20}$ aralkyl, such as benzyl, α-methylbenzyl, α, α-dimethylbenzyl and α-ethylbenzyl, may be given.

As examples for the optionally substituted aryl described above, an aromatic hydrocarbon, such as 1-naphthyl and 2-naphthyl, an oxygen-containing heterocycle, such as furyl, pyranyl and dioxyolanyl, a sulfur-containing heterocycle, such as thienyl, and a saturated or unsaturated nitrogen-containing heterocycle, such as pyrrolyl, imidazolyl, pyrazolyl, oxazolyl, isoxazolyl, triazolyl, thiazolyl, isothiazolyl, pyridyl, pyridazyl, pyrazinyl, benzimidazolyl, benzopyrazolyl, benzothiazolyl, quinolyl, antranyl, indonyl and phenanthrenyl, may be given.

Rb represents a group represented by any of the general formulae (3) through (6).

R1CO(R2)N— (3)

R1CO(R1'CO)N— (4)

R1CO(R1'SO$_2$)N— (5)

R1SO$_2$(R2)N— (6)

In the general formulae described above, R1, R1' and R2 each independently represent hydrogen, optionally substituted alkyl, optionally substituted alkoxy, optionally substituted alkenyl, optionally substituted aralkyl, optionally substituted aralkyloxy, optionally substituted aryl or optionally substituted aryloxy. Alternatively, R1 and R2 or R1 and R1' may be united to jointly form a $C_{5-8}$ membered heterocycle.

As definite examples for R1, R1' and R2 in the general formulae for Rb described above, hydrogen, $C_{1-10}$ alkyl and $C_{3-8}$ cycloalkyl, such as methyl, ethyl, propyl, isopropyl, butyl, sec-butyl, tert-butyl, pentyl, isopentyl, neopentyl, t-pentyl, hexyl, heptyl, cyclopropyl, cyclobutyl, cyclopentyl and cyclohexyl, optionally substituted aryl, such as phenyl, 2-methylphenyl, 2-ethylphenyl, 2-isopropylphenyl, 2-t-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-t-butylphenyl, 4-vinylphenyl, cumenyl, mesityl, xylyl, 1-naphthyl, 2-naphthyl, anthryl, phenanthryl and indenyl, optionally substituted $C_{7-10}$ aralkyl, such as 4-chlorobenzyl and α-methylbenzyl, $C_{2-10}$ alkenyl, such as vinyl, allyl and crotyl, $C_{1-10}$ alkoxy and $C_{3-8}$ cycloalkoxy, such as methoxy, ethoxy, propoxy, isopropoxy, butoxy, isobutoxy, t-butoxy, pentyloxy, isopentyloxy, neopentyloxy, t-pentyloxy, hexyloxy, cyclohexyloxy and heptyloxy, aryloxy, such as phenoxy, 2-methylphenoxy, 2-ethylphenoxy, 2-isopropylphenoxy, 2-t-butylphenoxy, 2-methoxyphenoxy, 2-chlorophenoxy, 2-vinylphenoxy, 3-methylphenoxy, 3-ethylphenoxy, 3-isopropylphenoxy, 3-methoxyphenoxy, 3-chlorophenoxy, 3-vinylphenoxy, 4-methylphenoxy, 4-ethylphenoxy, 4-isopropylphenoxy, 4-t-butylphenoxy, 4-vinylphenoxy, 1-naphthoxy and 2-naphthoxy, and optionally substituted $C_{7-20}$ aralkyl, such as benzyloxy, 4-chlorobenzyloxy and 4-methylbenzyloxy, may be given.

Further, R1 and R1' or R1 and R2 may be united to form a nitrogen-containing heterocycle. As examples for the nitrogen-containing heterocycle, an imide, such as succinimide, maleimide, phthalimide, 1,2-cyclohexane carboximide, 2,4,6-trioxopiperidine and α-pyridone, may be given.

As more definite examples for Rb, acylamino, such as formylamino, acetylamino, propionylamino, butylylamino, isobutylylamino, benzoylamino, 4-methylbenzoylamino, 2-chlorobenzoylamino, 3-methoxybenzoylamino and 2-chloro-4-methylbenzoylamino, diacylamino, such as diacetylamino and dibenzoylamino, N-alkyl-N-acylamino, such as N-formyl-N-methylamino, N-acetyl-N-methylamino, N-benzoyl-N-methylamino, N-acetyl-N-ethylamino, N-benzoyl-N-ethylamino, N-acetyl-N-benzylamino, N-benzoyl-N-benzylamino and 4-methylbenzoylmethylamino, N-aryl-N-acylamino, such as N-acetyl-N-phenylamino, N-acetyl-N-4-methylphenylamino, N-acetyl-N-2-chlorophenylamino, N-acetyl-N-2,4-dichlorophenylamino, N-benzyl-N-phenylamino, N-benzyl-N-4-methylphenylamino, N-benzyl-N-2-chlorophenylamino and N-benzyl-N-2,4-dichlorophenylamino, alkoxycarbonylamino, such as methoxycarbonylamino, ethoxycarbonylamino, propoxycarbonylamino, isopropoxycarbonylamino, n-butoxycarbonylamino and t-butoxycarbonylamino, aryloxycarbonylamino, such as benzyloxycarbonylamino, phenoxycarbonylamino, 2-methylphenoxycarbonylamino, 3-methylphenoxycarbonylamino, 4-methylphenoxycarbonylamino, 2-methoxyphenoxycarbonylamino, 3-methoxyphenoxycarbonylamino, 4-methoxyphenoxycarbonylamino, 2-chlorophenoxycarbonylamino, 3-chlorophenoxycarbonylamino and 4-chlorophenoxycarbonylamino, N-alkoxycarbonyl-N-alkylamino, such as N-methoxycarbonyl-N-methylamino, N-ethoxycarbonyl-N-methylamino, N-methoxycarbonyl-N-ethylamino, N-ethoxycarbonyl-N-ethylamino, N-propoxycarbonyl-N-propylamino, N-isopropoxycarbonyl-N-methylamino, N-butoxycarbonyl-N-ethylamino, N-t-butoxycarbonyl-N-methylamino and N-t-butoxycarbonyl-N-butoxyamino, N-alkoxycarbonyl-N-arylamino, such as N-methoxycarbonyl-N-phenylamino, N-ethoxycarbonyl-N-phenylamino, N-propoxycarbonyl-N-phenylamino, N-isopropoxycarbonyl-N-phenylamino, N-butoxycarbonyl-N-phenylamino and N-t-butoxycarbonyl-N-phenylamino, alkylsulfonylamino, such as methylsulfonylamino, ethylsulfonylamino, propylsulfonylamino, isopropylsulfonylamino, butylsulfonylamino and t-butylsulfonylamino, N-arylsulfonylamino, such as phenylsulfonylamino, 4-methylphenylsulfonylamino, 2-chlorophenylsulfonylamino and 2,4-dichlorophenylsulfonylamino, N-alkyl-alkylsulfonylamino and N-alkyl-substituted-phenylsulfonylamino, such as N-methyl-methylsulfonylamino, N-ethyl-methylsulfonylamino, N-propyl-methylsulfonylamino, N-isopropyl-methylsulfonylamino, N-benzyl-methylsulfonylamino, N-butyl-methylsulfonylamino, N-methyl-ethylsulfonylamino, N-ethyl-ethylsulfonylamino, N-methyl-propylsulfonylamino, N-ethyl-propylsulfonylamino, N-methyl-isopropylsulfonylamino, N-ethyl-isopropylsulfonylamino, N-methyl-butylsulfonylamino, N-ethyl-butylsulfonylamino, N-methyl-t-butylsulfonylamino, N-ethyl-t-butylsulfonylamino, N-methyl-phenylsulfonylamino, N-ethyl-phenylsulfonylamino, N-benzyl-phenylsulfonylamino, N-methyl-4-methylphenylsulfonylamino, N-benzyl-4-methylphenylsulfonylamino, N-ethyl-2-chlorophenylsulfonylamino and N-methyl-2,4-dichlorophenylsulfonylamino, N-aryl-alkylsulfonylamino and N-aryl-substituted-phenylsulfonylamino, such as N-phenyl-methylsulfonylamino, N-phenyl-ethylsulfonylamino, N-phenyl-propylsulfonylamino, N-phenyl-isopropylsulfonylamino, N-phenyl-butylsulfonylamino, N-phenyl-t-butylsulfonylamino, N-phenyl-phenylsulfonylamino, N-phenyl-4-methylphenylsulfonylamino, N-phenyl-2-chlorophenylsulfonylamino and N-phenyl-2,4-dichlorophenylsulfonylamino, and an imide, such as succinimidoyl, maleimideoyl, phthalimidoyl, 3-methylphthalimidoyl, 4-methylphthalimidoyl, 4-n-butylphthalimidoyl, 4-chlorophthalimidoyl, tetramethylphthalimidoyl, 1,2-cyclohexanecarboximidoyl, 2,4,6-trioxopiperidine-1-yl and α-pyridone-1-yl , may be given.

It is preferable that the optically active transition metal compound used in the process according to the present invention is a homogeneous system optically active hydrogenation catalyst. As the homogeneous system optically active hydrogenation catalyst, it is preferable to use a complex of a transition a metal which belongs to VIII-group of the periodic law table, such as Ru, Rh, Ir and Pt. Such optically active transition metal compounds may be synthesized or obtained according to the process set forth in Angew. Chem. Int. Ed., 37, 1703 (1998) or the like.

It is preferable that the homogeneous system optically active hydrogenation catalyst is one represented by the following general formula (7);

$$MaXY(Px)_m(Nx)_n \qquad (7)$$

wherein Ma represents a metal atom belonging to VIII-group, X and Y each independently represent hydrogen, halogeno, hydroxy or alkoxy, Px represents phosphine ligand, Nx represents amine ligand, provided that at least either Px or Nx is optically active, and m and n each independently represent 0 or an integer of 1 through 4.

In the general formula (7), it is preferable that Ma is a metal belonging to VIII-group, such as Ru, Rh, Ir and Pt. In particular, it is most preferable that Ma is a complex of Ru in view of stability of the complex and the supply availability.

In the general formula (7), X and Y each independently represent an anionic group including hydrogen, halogeno, such as fluorine, chlorine and bromine, hydroxy, alkoxy, such as methoxy, ethoxy, propoxy, isopropoxy and butoxy.

As Px as a phosphine ligand, unidentate ligand of phosphorus represented by a general formula of $PR_AR_BR_C$, bidentate ligand of phosphorus represented by a general formula of $R_DR_EP$—W—$PR_FR_G$ and the like may be given.

In the general formula $PR_AR_BR_C$, $R_A$, $R_B$ and $R_C$ each independently represent alkyl, optionally substituted phenyl, cycloalkyl or the like, or alternatively any two of $R_A$, $R_B$ and $R_C$ may be united to form an optionally substituted alicycle group.

When the phosphorus compound represented by the general formula of $PR_AR_BR_C$ is optically active, at least one of $R_A$, $R_B$ and $R_C$ is optically active or phosphorus atom substituted with three different substituents is optically active.

In the general formula of $R_DR_EP$—W—$PR_FR_G$, RD, RE, RF and RG each independently alkyl, optionally substituted phenyl or cycloalkyl, or alternatively RD and RE or RF and RG may be united to form optionally substituted alicyclic group. W represents $C_{1-10}$ hydrocarbon, cyclohydrocarbon, aryl, unsaturated hydrocarbon or the like.

As examples for the unidentate ligand represented by the general formula of $PR_AR_BR_C$ described above, a tertiary phosphine, such as trimethylphosphine, triethylphosphine, tributylphosphine, triphenylphosphine, tricyclohexylphosphine, tri(p-tolyl)phosphine, diphenylmethylphosphine, dimethylphenylphosphine, isopropylmethylphosphine, cyclohexyl(O-anisyl)-methylphosphine, 1-[2-(diphenylphosphino)ferrocenyl] ethyl methyl ether and 2-(diphenylphosphino)-2'-methoxy-1,1'-binaphthyl, may be preferably given. Further, a phosphine ligand represented by the general formula of PR$_A$R$_B$R$_C$ wherein the substituents for R$_A$, R$_B$ and R$_C$ are different groups from one another may be used as well.

As examples for the racemic or optically active bidentate phosphine ligand represented by the general formula of R$_D$R$_E$P—W—PR$_F$R$_G$ described above, bidentated tertiary phosphine, such as bis-diphenylphosphinomethane, bis-diphenylphosphinoethane, bis-diphenylphosphinopropane, bis-diphenylphosphinobutane, bis-dimethylphosphinoethane, and bis-dimethylphosphinopropane, and the like may be preferably given.

Further, as examples for the commercially available bidentate phosphine ligand, BINAP: 2,2'-bis-(diphenylphosphino)-1,1'-binaphthyl, BINAP derivative containing a substituent, such as alkyl and aryl, on the naphthyl ring, BINAP derivative containing 1–5 substituents, such as alkyl, on the benzene ring bonding to a phosphorus atom, such as H8BINAP and BINAP, Xylyl-BINAP: 2,2'-bis-(di-3,5-xylylphosphino)-1,1'-binaphthyl), BICHEP: 2,2'-bis-(dicyclohexylphosphino)-6,6'-dimethyl-1,1'-biphenyl, BPPFA: 1-[1', 2-bis-(diphenylphosphino) ferrosenyl]ethyldiamine, CHIRAPHOS 2,3-bis-(diphenylphosphino)butane, CYCPHOS: 1-cyclohexyl-1,2-bis-(diphenylphosphino)ethane, DEGPHOS: 1-substituted-3,4-bis(diphenylphosphino)pyrrolidine, DIOP: 2,3-O-isopropylpyridene-2,3-dihydroxy-1,4-bis-(diphenylphosphino)butane, DIPAMP: 1,2-bis[(O-methoxyphenyl)phenylphosphino]ethane, DuPHOS: (Substituted-1,2-bis(phosphorano)benzene), NORPHOS: 5,6-bis-(diphenylphosphino)-2-norbornene, PNNP: N,N'-bis-(diphenylphosphino)-N,N'-bis-[1-phenylethyl]ethylene diamine, PROPHOS: 1,2-bis-(diphenylphosphino)propane, KEWPHOS: 2,4-bis-(diphenylphosphino)pentane, and the like may be given. In addition, BINAP derivatives substituted with fluorine-containing substituent and the like may be used as well. There is no limitation for the phosphine ligand to be used in the present invention as far as it may stably form a metal complex.

As the amine ligand represented by Nx, a nitrogen-containing unidetate ligand represented by a general formula of NR$_H$R$_I$R$_J$, a diamine ligand represented by a general formula of R$_K$R$_L$N—X—NR$_M$R$_N$ and the like may be used.

In the general formula, NR$_H$R$_I$R$_J$ described above, R$_H$, R$_I$ and R$_J$ each independently represent hydrogen, alkyl, aryl or unsaturated hydrocarbon, or alternatively any two of R$_H$, R$_I$ and R$_J$ may be united to jointly form an optionally substituted alicyclic group. Further, at least one of R$_H$, R$_I$ and R$_J$ may be an optically active group.

In the general formula of R$_K$R$_L$N—X—NR$_M$R$_N$ described above, R$_K$, R$_L$, R$_M$ and R$_N$ each independently represent hydrogen, alkyl, aryl or unsaturated hydrocarbon, or alternatively R$_K$ and R$_L$ or R$_M$ and R$_N$ may be united to jointly form an optionally substituted alicyclic group or a nitrogen-containing heterocycle, and X represents C$_{1-5}$ alkyl, cycloalkyl ary or unsaturated hydrocarbon.

As examples for the monoamine ligand represented by the general formula of NR$_H$R$_I$R$_J$ described above, monoamine compounds, such as methylamine, ethylamine, propylamine, butylamine, pentylamine, hexylamine, cyclopentylamine, cyclohexylamine, benzylamine, dimethylamine, diethylamine, dipropylamine, dihexylamine, dicyclopentylamine, dicyclohexylamine, dibenzylamine, diphenylamine, phenylethylamine, proline and piperidine, may be given. In addition thereto, optically active monoamine compounds, such as optically active phenylethylamine, naphthylethylamine, cyclohexylamine and cycloheptylethylene diamine, may be examples for the optically active monoamine ligand.

As examples for the diamine ligand represented by the general formula of R$_K$R$_L$N—X—NR$_M$R$_N$ described above, methylene diamine, ethylene diamine, 1,2-diaminopropane, propylene diamine, 1,3-diaminopropane, 1,4-diaminobutane, 2,3-diaminobutane, 1,2-cyclopentane diamine, 1,2-cyclohexane diamine, N-methyl ethylene diamine, N,N'-dimethyl ethylene diamine, N,N,N'-trimethyl ethylene diamine, N,N,N',N'-tetramethyl ethylene diamine, o-phenylene diamine, p-phenylene diamine and the like may be given. Furthermore, optically active diamines may be used as the diamine ligand as well.

As examples for the optically active diamine compounds described above, 1,2-diphenyl ethylene diamine, 1,2-cyclohexane diamine, 1,2-cycloheptane diamine, 2,3-dimethylbutane diamine, 1-methyl-2,2-diphenyl ethylene diamine, 1-isobutyl-2,2-diphenyl ethylene diamine, 1-isopropyl-2,2-diphenyl ethylene diamine, 1-methyl-2,2-di(p-methoxyphenyl)ethylene diamine, 1-isobutyl-2,2-di(p-methoxyphenyl)ethylene diamine, 1-isopropyl-2,2-di(p-methoxyphenyl)ethylene diamine, 1-benzyl-2,2-di(p-methoxyphenyl) ethylene diamine, 1-methyl-2,2-dinaphthyl ethylene diamine, 1-isobutyl-2,2-dinaphthyl ethylene diamine, 1-isopropyl-2,2-dinaphthyl ethylene diamine and the like may be given.

The optically active diamine compounds usable in the process of the present invention are not limited to the optically active diamine derivatives as described above, and optically active derivatives of propane diamine, butane diamine, phenylene diamine, cyclohexane diamine and the like may be used as well. There is no limitation for the amine ligand to be used in the process of the present invention as far as it can stably form a metal complex.

In the present invention, the amount of the homogeneous system optically active hydrogenation catalyst to be used in the process shall differ depending upon the type of the reaction substrate, reaction container, economical condition, etc., however, the amount is normally in a range of from 1/100 to 1/10,000,000 as a molar ratio relative to a carbonyl compound as the reaction substrate, and more preferably in a range of from 1/200 to 1/100,000 as a molar ratio.

As the base used in the process of the present invention, it is preferable to use a compound represented by a general formula (8);

$$Mb_{m'}Z_n \quad (8)$$

wherein Mb represents an alkali metal ion or an alkaline earth metal ion, Z represents OH$^-$, RO$^-$, wherein R represents C$_{1-6}$ alkyl, an aromatic anion, HS$^-$ or CO3$^{2-}$, and m' and n' represent an integer of 1 through 3.

As examples for the base described above, KOH, KOCH$_3$, KOCH(CH$_3$)$_2$, KOC(CH$_3$)$_3$, KC$_{10}$H$_8$, NaOH, NaOCH$_3$, LiOH, LiOCH$_3$, LiOCH(CH$_3$)$_2$, Mg(OC$_2$H$_5$)$_2$, NsSH, K$_2$CO$_3$, Cs$_2$CO$_3$ and the like may be given. In addition, quaternary ammonium compounds may be also used as the base in the process of the present invention.

The amount of the base to be used in the process is normally 0.5 equivalent or more relative to the amount of the optically active transition metal compound, and more preferably 2 equivalents or more, when appropriate.

BEST MODE FOR CARRYING OUT THE INVENTION

The reaction in the process of the present invention is carried out by dissolving a substrate, which is an α-aminocarbonyl compound represented by the general formula (1), into an inactive solvent and applying hydrogen or a hydrogen donor for the reaction in the presence of an optically active transition metal compound and a base in a prefixed amount.

As the solvent usable in the reaction, any solvent which is inactive and capable of dissolving the reaction material (substrate) and a catalyst may be used without limitation. As examples for the solvent, an aromatic hydrocarbon, such as benzene, toluene and xylene, an aliphatic hydrocabon, such as pentane, hexane and octane, halogen-containing hydrocarbon, such as methylene chloride, chloroform and carbon tetrachloride, an ether, such as ether and tetrahydrofuran, an alcohol, such as methanol, ethanol, 2-propanol, butanol and benzyl alcohol, and an organic solvent containing hateroatom, such as acetonitrile, DMF (N,N-dimethylformamide), N-methyl pyrrolidone, pyridine and DMSO (domethylsulfoxide), may be given.

Among the examples for the solvent described above, it is particularly preferable to use an alcohol since the desired reaction product is an alcohol. Although the exampled solvent alone is usable, the solvents may be used in combination as well.

The amount of the solvent used in the reaction is determined in connection with the solubility of the reaction substrate and economical condition. For example, when 2-propanol is used as the solvent, the reaction may be proceeded at the substrate concentration range of from lower than 1% to almost no solvent condition, however, the solvent is preferably used at a concentration range of from 20 to 50 wt %.

The reaction is carried out in the presence of either hydrogen gas or a hydrogen donor. When hydrogen gas is used, it is preferable to maintain hydrogen pressure in the reaction system within a range of from 1 to 200 atmospheric pressure, and more preferably from 3 to 100 atmospheric pressure. As examples for the hydrogen donor described above, hydride complex, hydrogen occluded alloy and the like may be given.

The reaction temperature should be maintained in a range of from −30 to 200° C. while paying attention to the reaction speed, and more preferably in a range of from 15 to 100° C. The reaction is normally completed in a period of from several minutes to 10 hours depending upon the reaction condition, such as reaction substrate concentration, temperature and pressure.

Besides, when producing the optically active amino alcohol represented by the general formula (2) in an industrial scale, the reaction may be carried out by either batch system or continuous system.

The examples for the compounds represented by the general formula (2) to be produced according to the process of the present invention and the starting material compounds represented by the general formula (1) are shown in the following table.

In the table below, Et represents ethyl, Pr represents propyl, Bu represents butyl and Ph represents phenyl.

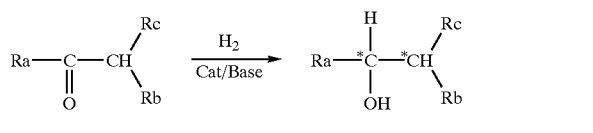

TABLE 1

| Compound No. | Ra | Rb | Rc |
|---|---|---|---|
| I-1 | Me | NHCOO(t-Bu) | H |
| I-2 | Et | NHCOO(t-Bu) | H |
| I-3 | i-Pr | NHCOO(t-Bu) | H |
| I-4 | n-$C_6H_{13}$ | NHCOO(t-Bu) | H |
| I-5 | c-$C_6H_{11}$ | NHCOO(t-Bu) | H |
| I-6 | $CH_2$=CH | NHCOO(t-Bu) | H |
| I-7 | PhCH=CH | NHCOO(t-Bu) | H |
| I-8 | Ph | NHCOO(t-Bu) | H |
| I-9 | 2-Me-Ph | NHCOO(t-Bu) | H |
| I-10 | 3-Me-Ph | NHCOO(t-Bu) | H |
| I-11 | 4-Me-Ph | NHCOO(t-Bu) | H |
| I-12 | 4-Cl-Ph | NHCOO(t-Bu) | H |
| I-13 | 4-MeO-Ph | NHCOO(t-Bu) | H |
| I-14 | 3-$NO_2$-Ph | NHCOO(t-Bu) | H |
| I-15 | 1-naphthyl | NHCOO(t-Bu) | H |
| I-16 | 2-pyridyl | NHCOO(t-Bu) | H |
| I-17 | 2-furyl | NHCOO(t-Bu) | H |
| I-18 | 3-pyrazolyl | NHCOO(t-Bu) | H |
| I-19 | 2-oxazolyl | NHCOO(t-Bu) | H |
| I-20 | 2-thiazolyl | NHCOO(t-Bu) | H |
| I-21 | 2-imidazolyl | NHCOO(t-Bu) | H |
| I-22 | 2-pyrrolyl | NHCOO(t-Bu) | H |
| I-23 | 2-thienyl | NHCOO(t-Bu) | H |
| I-24 | Benzimisazole-2-yl | NHCOO(t-Bu) | H |
| I-25 | Me | NHCOO(t-Bu) | Me |
| I-26 | c-$C_6H_{11}$ | NHCOO(t-Bu) | Me |
| I-27 | $CH_2$=CH | NHCOO(t-Bu) | Me |
| I-28 | PhCH=CH | NHCOO(t-Bu) | Me |
| I-29 | Ph | NHCOO(t-Bu) | Me |
| I-30 | 2-Me-Ph | NHCOO(t-Bu) | Me |
| I-31 | 3-Me-Ph | NHCOO(t-Bu) | Me |
| I-32 | 4-Me-Ph | NHCOO(t-Bu) | Me |
| I-33 | 4-Cl-Ph | NHCOO(t-Bu) | Me |
| I-34 | 4-MeO-Ph | NHCOO(t-Bu) | Me |
| I-35 | 3-$NO_2$-Ph | NHCOO(t-Bu) | Me |
| I-36 | 1-naphthyl | NHCOO(t-Bu) | Me |
| I-37 | 2-pyridyl | NHCOO(t-Bu) | Me |
| I-38 | 2-furyl | NHCOO(t-Bu) | Me |
| I-39 | 3-pyrazolyl | NHCOO(t-Bu) | Me |
| I-40 | 2-oxazolyl | NHCOO(t-Bu) | Me |
| I-41 | 2-thoazolyl | NHCOO(t-Bu) | Me |
| I-42 | 2-imidazolyl | NHCOO(t-Bu) | Me |
| I-43 | 2-pyrrolyl | NHCOO(t-Bu) | Me |
| I-44 | 2-thienyl | NHCOO(t-Bu) | Me |
| I-45 | benzimidazole-2-yl | NHCOO(t-Bu) | Me |
| I-46 | Me | NHCOO(t-Bu) | Ph |
| I-47 | c-$C_6H_{11}$ | NHCOO(t-Bu) | Ph |
| I-48 | $CH_2$=CH | NHCOO(t-Bu) | Ph |
| I-49 | PhCH=CH | NHCOO(t-Bu) | Ph |
| I-50 | Ph | NHCOO(t-Bu) | Ph |
| I-51 | Ph | NHCOO(t-Bu) | CH=$CH_2$ |
| I-52 | Ph | NHCOO(t-Bu) | $CH_2$CH=$CH_2$ |
| I-53 | Me | phthalimidoyl | H |
| I-54 | c-$C_6H_{11}$ | phthalimidoyl | H |
| I-55 | $CH_2$=CH | phthalimidoyl | H |
| I-56 | PhCH=CH | phthalimidoyl | H |
| I-57 | Ph | phthalimidoyl | H |
| I-58 | 2-Me-Ph | phthalimidoyl | H |
| I-59 | 3-Me-Ph | phthalimidoyl | H |
| I-60 | 4-Me-Ph | phthalimidoyl | H |
| I-61 | 4-Cl-Ph | phthalimidoyl | H |
| I-62 | 4-Meo-Ph | phthalimidoyl | H |
| I-63 | 3-N02-Ph | phthalimidoyl | H |
| I-64 | 1-naphthyl | phthalimidoyl | H |
| I-65 | 2-pyridyl | phthalimidoyl | H |
| I-66 | 2-furyl | phthalimidoyl | H |
| I-67 | 3-pyrazolyl | phthalimidoyl | H |
| I-68 | 2-oxazolyl | phthalimidoyl | H |
| I-69 | 2-thiazolyl | phthalimidoyl | H |
| I-70 | 2-imidazolyl | phthalimidoyl | H |
| I-71 | 2-pyrrolyl | phthalimidoyl | H |
| I-72 | 2-thienyl | phthalimidoyl | H |
| I-73 | benzimidazole-2-yl | phthalimidoyl | H |
| I-74 | Me | phthalimidoyl | Me |
| I-75 | c-$C_6H_{11}$ | phthalimidoyl | Me |

TABLE 1-continued

| Compound No. | Ra | Rb | Rc |
| --- | --- | --- | --- |
| I-76 | CH$_2$=CH | phthalimidoyl | Me |
| I-77 | PhCH=CH | phthalimidoyl | Me |
| I-78 | Ph | phthalimidoyl | Me |
| I-79 | 2-Me-Ph | phthalimidoyl | Me |
| I-80 | 3-Me-Ph | phthalimidoyl | Me |
| I-81 | 4-Me-Ph | phthalimidoyl | Me |
| I-82 | 4-Cl-Ph | phthalimidoyl | Me |
| I-83 | 4-MeO-Ph | phthalimidoyl | Me |
| I-84 | 3-NO$_2$-Ph | phthalimidoyl | Me |
| I-85 | 1-naphthyl | phthalimidoyl | Me |
| I-86 | 2-pyridyl | phthalimidoyl | Me |
| I-87 | 2-furyl | phthalimidoyl | Me |
| I-88 | 3-pyrazolyl | phthalimidoyl | Me |
| I-89 | 2-oxazolyl | phthalimidoyl | Me |
| I-90 | 2-thiazolyl | phthalimidoyl | Me |
| I-91 | 2-imidazolyl | phthalimidoyl | Me |
| I-92 | 2-pyrrolyl | phthalimidoyl | Me |
| I-93 | 2-thienyl | phthalimidoyl | Me |
| I-94 | benzimidazole-2-yl | phthalimidoyl | Me |
| I-95 | Me | phthalimidoyl | Ph |
| I-96 | c-C$_6$H$_{11}$ | phthalimidoyl | Ph |
| I-97 | CH$_2$=CH | phthalimidoyl | Ph |
| I-98 | PhCH=CH | phthalimidoyl | Ph |
| I-99 | Ph | phthalimidoyl | Ph |
| I-100 | Ph | phthalimidoyl | CH=CH$_2$ |
| I-101 | Ph | phthalimidoyl | CH$_2$CH=CH$_2$ |
| I-102 | PhCH=CH | NHCOOMe | H |
| I-103 | Ph | NHCOOMe | H |
| I-104 | PhCH=CH | NHCOOMe | Me |
| I-105 | Ph | NHCOOMe | Me |
| I-106 | PhCH=CH | NHCOOMe | Ph |
| I-107 | Ph | NHCOOMe | Ph |
| I-108 | Ph | NHCOOMe | CH$_2$=CH |
| I-109 | PhCH=CH | NHCOOMe | H |
| I-110 | Ph | NHCOOMe | H |
| I-111 | PhCH=CH | NHCOOMe | Me |
| I-112 | Ph | NHCOOMe | Me |
| I-113 | PhCH=CH | NHCOOMe | Ph |
| I-114 | Ph | NHCOOMe | Ph |
| I-115 | Ph | NHCOOMe | CH$_2$=CH |
| I-116 | PhCH=CH | NHCOO(i-Pr) | H |
| I-117 | Ph | NHCOO(i-Pr) | H |
| I-118 | PhCH=CH | NHCOO(i-Pr) | Me |
| I-119 | Ph | NHCOO(i-Pr) | Me |
| I-120 | PhCH=CH | NHCOO(i-Pr) | Ph |
| I-121 | Ph | NHCOO(i-Pr) | Ph |
| I-122 | Ph | NHCOO(i-Pr) | CH$_2$=CH |
| I-123 | Ph | NHCOOCH$_{2Ph}$ | H |
| I-124 | Ph | NHCOOCH$_{2Ph}$ | Me |
| I-125 | Ph | NHCOOCH$_{2Ph}$ | Ph |
| I-126 | PhCH=CH | N(CH$_3$)COOEt | H |
| I-127 | Ph | N(CH$_3$)COOEt | H |
| I-128 | PhCH=CH | N(CH$_3$)COOEt | Me |
| I-129 | Ph | N(CH$_3$)COOEt | Me |
| I-130 | PhCH=CH | N(CH$_3$)COOEt | Ph |
| I-131 | Ph | N(CH$_3$)COOEt | Ph |
| I-132 | Ph | N(CH$_3$)COOEt | CH$_2$=CH |
| I-133 | PhCH=CH | N(CH$_3$)COO(i-Pr) | H |
| I-134 | Ph | N(CH$_3$)COO(i-Pr) | H |
| I-135 | PhCH=CH | N(CH$_3$)COO(i-Pr) | Me |
| I-136 | Ph | N(CH$_3$)COO(i-Pr) | Me |
| I-137 | PhCH=CH | N(CH$_3$)COO(i-Pr) | Ph |
| I-138 | Ph | N(CH$_3$)COO(i-Pr) | Ph |
| I-139 | Ph | N(CH$_3$)COO(i-Pr) | CH$_2$=CH |
| I-140 | Ph | N(CH$_3$)COO(t-Bu) | H |
| I-141 | PhCH=CH | N(CH$_3$)COO(t-Bu) | Me |
| I-142 | Ph | N(CH$_3$)COO(t-Bu) | Me |
| I-143 | PhCH=CH | N(CH$_3$)COO(t-Bu) | Ph |
| I-144 | Ph | N(CH$_3$)COO(t-Bu) | Ph |
| I-145 | PhCH=CH | NHCOCH$_3$ | H |
| I-146 | Ph | NHCOCH$_3$ | H |
| I-147 | PhCH=CH | NHCOCH$_3$ | Me |
| I-148 | Ph | NHCOCH$_3$ | Me |
| I-149 | PhCH=CH | NHCOCH$_3$ | Ph |
| I-150 | Ph | NHCOCH$_3$ | Ph |
| I-151 | PhCH=CH | NHCOPh | H |
| I-152 | Ph | NHCOPh | H |
| I-153 | PhCH=CH | NHCOPh | Me |
| I-154 | Ph | NHCOPh | Me |
| I-155 | PhCH=CH | NHCOPh | Ph |
| I-156 | Ph | NHCOPh | Ph |
| I-157 | PhCH=CH | N(CH$_3$)COCH$_3$ | H |
| I-158 | Ph | N(CH$_3$)COCH$_3$ | H |
| I-159 | PhCH=CH | N(CH$_3$)COCH$_3$ | Me |
| I-160 | Ph | N(CH$_3$)COCH$_3$ | Me |
| I-161 | PhCH=CH | N(CH$_3$)COCH$_3$ | Ph |
| I-162 | Ph | N(CH$_3$)COCH$_3$ | Ph |
| I-163 | PhCH=CH | N(CH$_3$)COPh | H |
| I-164 | Ph | N(CH$_3$)COPh | H |
| I-165 | PhCH=CH | N(CH$_3$)COPh | Me |
| I-166 | Ph | N(CH$_3$)COPh | Me |
| I-167 | PhCH=CH | N(CH$_3$)COPh | Ph |
| I-168 | Ph | N(CH$_3$)COPh | Ph |
| I-169 | PhCH=CH | NHCOH | H |
| I-170 | Ph | NHCOH | H |
| I-171 | PhCH=CH | NHCOH | Me |
| I-172 | Ph | NHCOH | Me |
| I-173 | PhCH=CH | NHCOH | Ph |
| I-174 | Ph | NHCOH | Ph |
| I-175 | PhCH=CH | N(CH$_3$)COH | H |
| I-176 | Ph | N(CH$_3$)COH | H |
| I-177 | PhCH=CH | N(CH$_3$)COH | Me |
| I-178 | Ph | N(CH$_3$)COH | Me |
| I-179 | PhCH=CH | N(CH$_3$)COH | Ph |
| I-180 | Ph | N(CH$_3$)COH | Ph |
| I-181 | PhCH=CH | N(CH$_3$)COOMe | H |
| I-182 | Ph | N(CH$_3$)COOMe | H |
| I-183 | PhCH=CH | N(CH$_3$)COOMe | Me |
| I-184 | Ph | N(CH$_3$)COOMe | Me |
| I-185 | PhCH=CH | N(CH$_3$)COOMe | Ph |
| I-186 | Ph | N(CH$_3$)COOMe | Ph |
| I-187 | PhCH=CH | N(CH$_3$)SO2Me | H |
| I-188 | Ph | N(CH$_3$)SO2Me | H |
| I-189 | PhCH=CH | N(CH$_3$)SO2Me | Me |
| I-190 | Ph | N(CH$_3$)SO2Me | Me |
| I-191 | PhCH=CH | N(CH$_3$)SO$_2$Me | Ph |
| I-192 | Ph | N(CH$_3$)SO$_2$Me | Ph |
| I-193 | PhCH=CH | N(CH$_3$)SO$_2$4-Me-Ph) | H |
| I-194 | Ph | N(CH$_3$)SO$_2$4-Me-Ph) | H |
| I-195 | PhCH=CH | N(CH$_3$)SO$_2$4-Me-Ph) | Me |
| I-196 | Ph | N(CH$_3$)SO$_2$4-Me-Ph) | Me |
| I-197 | PhCH=CH | N(CH$_3$)SO$_2$4-Me-Ph) | Ph |
| I-198 | Ph | N(CH$_3$)SO$_2$4-Me-Ph) | Ph |

Now, the present invention is further explained in detail with referring the following examples.

EXAMPLE 1

Synthesis of (1S, 2S)-2-phthalimidoyl-1-phenylpropanol

2-Propanol in an amount of 8 ml, [(s)-xylyl-BINAP]Ru(II)Cl$_2$[(S,S)DPEN in an amount of 5.6 mg (0.005 mmol), 2 ml solution of 0.5N-tBuOK and 2-propanol and 2-phthalimidoylpropiophenone in an amount of 1.4 g (5.00 mmol) were placed in 100 ml volume autoclave under atmosphere of argon gas, and the autoclave was fed with hydrogen gas until the inside pressure reached to 10 atmospheric pressure. The mixture obtained as described above was stirred for 18 hours at 25° C., then dried and subjected to the analysis by means of silica gel column chromatography, where ethyl acetate was used as the eluate. The combined amount of fractions for the objective compound and the isomer were 1.11 g (Yield: 79%). The diastereomer ratio was determined from the chemical shift value of the terminal methyl group by employing 1H-NMR spectrum analysis. (δ of the syn-isomer was 1.47 and δ of the anti-isomer was 1.40.) After the analysis, it was found that the production ratio of the syn-isomer and the anti-isomer was 22.6 versus 1 (91%de). These diastereomers were further separated by means of silica gel column chromatography, where a mixture of hexane and ethyl acetate at a rate of 8/2 was used, and it was noted that the main product was (1S, 2S)-2-phthalimidoyl-1-phenylpropanol. The optical purity of said main product was analyzed as 96.0%de by means of high performance liquid chromatography (column: Chiralcell OJ, Eluate: hexane/ethanol=10/1, Flow rate: 1.0 ml/min., Wavelength for detection: 254 nm)

EXAMPLE 2

Synthesis of (S)-1-phenyl-2-(t-butoxycarbonylamino)ethanol i) Synthesis of α-(t-butoxycarbonylamino)acetophenone α-aminoacetophenone hydrochloride in an amount of 9.0 g (52.4 mmol), anhydrous $Boc_2O$ in an amount of 12.0 g (55.0 mmol) and 60 ml of chloroform were placed in a 200 ml flask, and potassium carbonate in an mount of 7.23 g (52.4 mmol) was further added into the flask at 0° C. while spending 5 minutes and stirring to subject the mixture to a reaction. Then, the mixture was added with water for an extraction, and the obtained chloroform layer was dried with magnesium sulfate. After filtration and condensation of the chloroform layer, the obtained residue was purified by means of column chromatography (hexane:ethyl acetate= 2:1). The obtained crystals were subjected to recrystallization with diethyl ether and then petroleum ether to obtain α-(t-butoxycarbonylamino)acetophenone in an amount of 8.1 g (34.4 mmol) at a yield of 66%.

ii) Synthesis of (S)-1-phenyl-2-(t-butoxycarbonylamino) ethanol

[(S)-xylyl-BINAP]$RuCl_2$(S,S)-DPEN in an amount of 5.2 mg (0.0046 mmol), α-(t-butoxycarbonylamino) acetophenone in an amount of 217 mg (0.923 mmol), 9.5 ml of dehydrated and distilled isopropanol and 0.46 ml (0.23 mmol) of 0.5N-isopropanol solution of t-butoxy potassium were placed into a 100 ml capacity autoclave under atmosphere of argon gas. By evacuating air from the autoclave, the air in the interior of the autoclave was substituted by hydrogen gas and the hydrogen pressure was adjusted to a level of 12 kgf/cm2. The mixture in the autoclave was stirred for 42 hours at am ambient temperature, and the reacted solution was filtrated with celite and condensed to quantitatively obtain (S)-1-phenyl-2-(t-butoxycarbonylamino) ethanol in an amount of 219 mg (0.923 mmol). The optical purity of the obtained compound was analyzed and found to be 96.6%ee by means of high performance liquid chromatography (Column: Chiralcell OJ, Eluate:hexane:ethanol= 20:1, Flow rate: 1.3 ml/min., Wavelength for detection: 210 nm).

EXAMPLE 3 i) Synthesis of 1-phenyl-2-(t-butoxycarbonylamino) propanol

α-(t-butoxycarbonylamino)propiophenone in an amount of 997 mg (4.00 mmol) and [(S)-xylyl-BINAP]$RuCl_2$(S,S)-DPEN in an amount of 22.4 mg (0.02 mmol) were dissolved into 18 ml of dehydrated and distilled isopropanol under atmosphere of argon gas. The obtained solution and 2.0 ml (1.0 mmol) of 0.5N-isopropanol solution of t-butoxy potassium were placed into an autoclave (capacity: 100 ml), the air in the autoclave was repeatedly evacuated and then substituted with hydrogen gas, and the hydrogen pressure in the autoclave was adjusted to a level of 12 kgf/cm2. After stirring the solution contained in the autoclave for 22 hours at an ambient temperature, the reacted solution was filtrated with celite and condensed to quantitatively obtain 1-phenyl-2-(t-butoxycarbonylamino)propanol in an amount of 1.05 g (4.00 mmol). The diastereoselectivity ratio of the obtained compound was determined by means of proton NMR (300MHz) and was found to be 38%de (syn: anti=31.69).

ii) Synthesis of 1-phenyl-2-aminopropanol 20 ml of 3N-hydrochloric acid solution and 10 ml of methanol were added into the above-described 1-phenyl-2-(t-butoxycarbonylamino)propanol in an amount of 1.05 g (4.00 mmol), and the resulting solution was stirred for an hour at an ambient temperature. Then, the methanol in the solution was distilled out, and the aqueous layer of the solution was separated by extraction with ethyl acetate. The aqueous layer was adjusted to alkaline state by adding aqueous solution of sodium hydroxide and was then extracted with chloroform. The obtained chloroform solution was dried with anhydrous magnesium sulfate and distilled under reduced pressure to obtain 1-phenyl-2-aminopropanol in an amount of 465 mg (2.48 mmol) at a yield of 77%.

iii) Determination of optical purity of 1-phenyl-2-aminopropanol

Benzoyl chloride in an amount of 349 mg (2.48 mmol) and triethylamine in an amount of 1.0 ml (7.3 mmol) were added into 10 ml of chloroform solution of the above-described 1-phenyl-2-aminopropanol in an amount of 465 mg (2.48 mmol). The resulting solution was stirred for 2 hours in ice bath and added with water to discontinue the reaction. After separation of the solution, the chloroform solution was dried with anhydrous magnesium sulfate and distilled out under reduced pressure to obtain 1-phenyl-2-benzoylaminopropane in crude state. The crude product was purified by means of silica gel column chromatography (hexane:ethyl acetate=3:1) to obtain anti-isomer of 1-phenyl-2-benzoylaminopropanol in an amount of 705 mg (2.42 mmol) at a yield of 97%. The optical purity of said anti-isomer was determined by means of high performance liquid chromatography (ethanol:hexane 1:30, flow rate: 1.0 ml/min., chiralcell OJ) and was found to be 95% ee as the purity of the (1S, 2R)-isomer. The optical purity of the syn-isomer was also determined and the purity was found to be 90% ee as the purity of the (1S, 2S)-isomer.

EXAMPLE 4

Synthesis of 1-phenyl-2-benzoylaminopropanol

1-Phenyl-2-benzoylaminopropane-1-one in an amount of 0.40 g (1.58 mmol) and [(S)-xylyl-BINAP]$RuCl_2$(S,S)-DPEN in an amount of 9.6 mg (0.01 mmol) were dissolved in 5 ml of dehydrated and distilled isopropanol under atmosphere of argon gas. 0.8 ml of 0.5M isopropanol solution of potassium hydroxide was dissolved into the obtained solution as described above, and the resulting solution was stirred for 22 hours at 35° C. under 10 atmospheric pressure of hydrogen gas. Isopropanol in the solution was distilled out under reduced pressure, and the solution was then added with water, extracted with ethyl acetate, washed with saturated saline solution, dried with magnesium sulfate and condensed to obtain a crude product. The crude product was subjected to separation by means of silica gel column chromatography to obtain the captioned compound in an amount of 0.38 g (Yield 94%). The diastereoselectivity ratio of the obtained compound was measured by means of using proton NMR (300 MHz) and was found to be syn:anti=65:35. The optical purity of the syn-isomer and the anti-isomer were determined by means of HPLC and the optical purity was 91% ee (1S, 2R) for the syn-isomer and 61% ee (1S, 2S) for the anti-isomer.

INDUSTRIAL USE OF INVENTION

According to the preparation process for optically active β-amino alcohols of the present invention, syn-steric optically active β-amino alcohols useful as an intermediate for pharmaceutical active ingredients and agricultural chemicals can be advantageously and highly selectively produced at a high yield in an industrial scale.

What is claimed is:

1. A process for preparing optically active β-amino alcohols represented by a general formula (2);

$$Ra—C^*H(OH)—C^*H(Rb)—Rc \qquad (2)$$

wherein Ra and Rc are each independently hydrogen, optionally substituted alkyl, optionally substituted cycloalkyl, optionally substituted alkenyl, optionally substituted aralkyl or optionally substituted aryl, Rb is one member selected from among groups represented by the following general formulae; (3) R1CO(R2)N—, and (4) R1CO(R1'CO)N—, wherein R1, R1' and R2 are each independently hydrogen, optionally substituted alkyl, optionally substituted alkoxy, optionally substituted cycloalkyl, optionally substituted cycloalkoxy, optionally substituted alkenyl, optionally substituted aralkyl, optionally substituted aralkyloxy, optionally substituted aryl or optionally substituted aryloxy, or alternatively R1 and R2 or R1 and R1' may be united to form a five- to eight-membered nitrogenous heterocycle, and C* is an asymmetric carbon atom, characterized by reacting a racemic α-aminocarbonyl compound represented by the general formula (1);

$$Ra—CO—CH(Rb)—Rc \qquad (1)$$

wherein Ra, Rb and Rc are each as defined above, with hydrogen in the presence of an optically active transition metal compound represented by a general formula (7);

$$MaXY(Px)m(Nx)n \qquad (7)$$

wherein Ma represents a metal atom belonging to VIII-group of the periodic law,

X and Y represent each independently hydrogen, halogeno, carboxyl, hydroxide or alkoxy, Px represents a phosphine ligand, Nx represents an amine ligand, at least one of Px and Nx is optically active, and m and n each independently represent 0 or an integer of 1 through 4 and a base.

2. The process for preparing optically active β-amino alcohols according to claim 1, wherein the base is a compound represented by a general formula (8);

$$Mbm'Zn' \qquad (8)$$

wherein Mb represents an alkali metal ion or an alkaline earth metal ion, Z represents $OH^-$, $RO^-$, wherein R represents $C_{1-6}$ alkyl, an aromatic anion, $HS^-$ or $CO3^{2-}$, and m' and n' each independently represent an integer of 1 through 3.

3. The process for preparing optically active β-amino alcohols according to claim 1, wherein the Nx is an amine ligand represented by the general formula;

$$R_K R_L N—X—NR_M R_N$$

$R_K$, $R_L$, $R_M$ and $R_N$ each independently represent hydrogen, alkyl, aryl or unsaturated hydrocarbon, or alternatively $R_K$ and $R_L$ or $R_M$ and $R_N$ may be united to jointly form an optionally substituted alicyclic group or a nitrogen-containing heterocycle, and X represents $C_{1-5}$ alkyl, cycloalkyl, aryl or unsaturated hydrocarbon.

* * * * *

UNITED STATES PATENT AND TRADEMARK OFFICE
CERTIFICATE OF CORRECTION

PATENT NO.    : 6,410,749 B1
DATED         : June 25, 2002
INVENTOR(S)   : Eiji Katayama et al.

It is certified that error appears in the above-identified patent and that said Letters Patent is hereby corrected as shown below:

<u>Title page,</u>
Item [75], Inventors, replace "city of all inventors" with -- Kanagawa, Japan --.

<u>Column 7,</u>
Line 54, replace "cycloalkyl, ary or" with -- cycloalkyl, aryl or --.

<u>Column 11,</u>
Table 1, Compound Nos. I-123, I-124, I-125, under heading Rb replace "NHCOOCH$_{2ph}$" with -- NHCOOCH$_2$Ph --

<u>Column 12,</u>
Table 1, Compound Nos. I-193 through I-198, under heading Rb replace "N(CH$_3$)SO$_2$4-Me-Ph)" with -- N(CH$_3$)SO$_2$(4-Me-Ph) --

Signed and Sealed this

Tenth Day of September, 2002

Attest:

*Attesting Officer*

JAMES E. ROGAN
*Director of the United States Patent and Trademark Office*